United States Patent [19]

Nagai et al.

[11] Patent Number: 4,841,083
[45] Date of Patent: Jun. 20, 1989

[54] LADDER POLYSILANES

[75] Inventors: Yoichiro Nagai, Yamato; Hideyuki Matsumoto, Kiryu, both of Japan

[73] Assignee: Mitsui Toatsu Chemicals, Incorporated, Tokyo, Japan

[21] Appl. No.: 199,805

[22] Filed: May 27, 1988

[30] Foreign Application Priority Data

Jun. 3, 1987 [JP] Japan .................................. 62-138287

[51] Int. Cl.$^4$ ............................ C07F 7/08; C07F 7/10; C07F 7/18
[52] U.S. Cl. .................................... 556/430; 556/413; 556/414; 556/422; 556/428; 423/324; 423/325; 423/341; 423/344; 423/347
[58] Field of Search ............... 556/413, 414, 422, 428, 556/430; 423/325, 341, 344, 347, 324

[56] References Cited

U.S. PATENT DOCUMENTS

| 4,704,444 | 11/1987 | Brown-Wusley et al. | 556/430 X |
| 4,727,171 | 2/1988 | Nagai et al. | 556/430 |
| 4,777,234 | 10/1988 | Litt et al. | 556/430 X |

FOREIGN PATENT DOCUMENTS

| 207829 | of 1984 | Japan | 556/412 |
| 207830 | of 1984 | Japan | 556/412 |
| 232910 | of 1984 | Japan | 556/412 |
| 210718 | of 1986 | Japan | 556/412 |
| 210719 | of 1986 | Japan | 556/412 |

OTHER PUBLICATIONS

Organometallics (1985), vol. 282, pp. 305 and 306.
Organometallics, 1983, 2, 1464–1466.
J. Organomet. Chem., 77, (1974), pp. C–13–C14.
J. Am. Ceramic Soc., 61, pp. 504–508 (1978).
Burkhard, Charles, A., J. Am. Chem. Soc., 71 (1949), 963–964.
West, Robert, et al., Science 214, (1981), 1343–1344.
J. Am. Chem. Soc., 104 (1982), 504–509.

Primary Examiner—Paul F. Shaver
Attorney, Agent, or Firm—Fisher, Christen & Sabol

[57] ABSTRACT

There is here disclosed a ladder polysilane represented by the general formula (I):

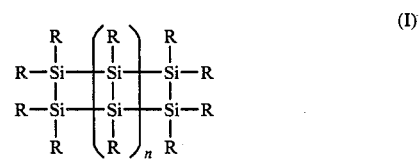

wherein n is a positive integer, and R is a halogen atom, a hydrogen atom, a hydroxyl group, an alkyl group, an alkenyl group, an aryl group or an alkoxy group having 20 or less carbon atoms, and the alkyl, alkenyl, aryl or alkoxy group may contain a functional group such as —COOH, —SO$_3$H, —NH$_2$, —NO$_2$, —NCO, —F, —Cl, —BR, —I or —OH. In addition, a method for preparing the aforesaid ladder polysilane is also disclosed here.

3 Claims, No Drawings

LADDER POLYSILANES

BACKGROUND OF THE INVENTION 1. (a) Field of the Invention

The present invention relates to ladder polysilanes which are novel compounds, and a method for preparing the same.

2. (b) Description of the Prior Art

In recent years, the technology of organic silicon chemistry has advanced actively and rapidly, and a variety of cyclopolysilanes having high strain become now already synthesized. For example, there are [(CH$_3$)$_2$Si]$_6$ in J. Am. Chem. Soc. 71, 963 (1949); [t-Bu(CH$_3$)Si]$_4$ (Bu is a butyl group) in J. Organomet. Chem., 77, C13 (1974); (Mes$_2$Si)$_2$ (Mes is a mesityl group) in Science, 214, 1343 (1981); (Ar$_2$Si)$_3$ (Ar is a 2,6-dimethylphenyl group) in J. Am. Chem. Soc., 104, 1152 (1982); [t-BuCH$_2$)$_2$Si]$_3$ and [t-BuCH$_2$)$_2$Si]$_2$ in Chem. Commun. 781 (1983); and (t-Bu$_2$Si)$_3$ and (t-Bu$_2$Si)$_2$ in *Organometallics* 1983, 2, 1464, and *Journal of Organometallic Chemistry*, 282 (1985) 305. In addition, examples of the cyclopolysilanes having silyl groups on side chains thereof include [[(CH$_3$)$_3$Si]$_2$Si]$_4$ in Organometallics, 1410 (1982), [[(C$_2$H$_5$)$_3$Si]$_2$Si]$_3$ in Japanese patent application No. 61-210718, and [[(C$_2$H$_5$)(CH$_3$)$_2$Si]$_2$Si]$_4$ in Japanese patent application No. 61-210719.

These high-strain cyclopolysilanes have great strain energy and are thermally reactive, and therefore they are used as reagents for reactions with various molecules. The Si—Si bond in the cyclopolysilane is easily decomposed by light irradiation (about 200 to 400 nm) to release silylene (=SiR$_2$), and thus by the utilization of this, various photoreactions can be carried out. In particular, the cyclopolysilane having the silyl groups on the side chains thereof contains many Si—Si bonds, and therefore it can be presumed that the photoreactivity of the cyclopolysilane is extremely high. Furthermore, the cyclopolysilanes which have undergone ring opening polymerization can be utilized in a wide range as raw materials for polymers and SiC ceramics and as photoresists, and for this reason, the cyclopolysilanes are expected.

Moreover, chain polysilanes represented by the formula

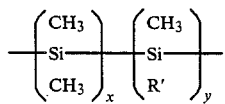

wherein x and y are each a positive integer, and R' is an alkyl group, a phenyl group or the like, having easy workability has been discovered of late [J. Am. Ceramic Soc., 61, 504 (1978)]. Since the chain polysilanes have electric conductivity and photosensitivity, development has been actively made to utilize them as functional materials such as photoresists, semiconductors and prepolymers for ceramics.

SUMMARY OF THE INVENTION

An object of the present invention is to provide a novel polysilane having a structure in which silicon atoms are arranged in the form of a ladder, and a method for preparing the novel polysilane by using easily available organic silicon compounds as starting materials.

The ladder polysilane of the present invention is represented by the following general formula (I):

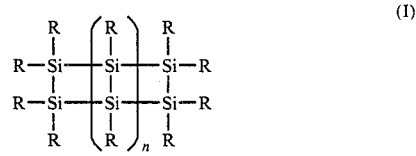

wherein n is a positive integer, and R is a halogen atom, a hydrogen atom, a hydroxyl group, an alkyl group, an alkenyl group, an aryl group or an alkoxy group having 20 or less carbon atoms, and the alkyl, alkenyl, aryl or alkoxy group may contain a functional group such as —COOH, —SO$_3$H, —NH$_2$, —NO$_2$, —NCO, —F, —Cl, —Br, —I or —OH.

DETAILED DESCRIPTION OF THE INVENTION

In a ladder polysilane represented by the general formula (I), typical examples of the R group include a chlorine atom, bromine atom, iodine atom, hydrogen atom, hydroxyl group, methyl group, ethyl group, n-propyl group, iso-propyl group, n-butyl group, iso-butyl group, t-butyl group, n-pentyl group, neo-pentyl group, n-hexyl group, n-octyl group, hexadecyl group, vinyl group, allyl group, n-butenyl group, phenyl group, toluyl group, naphthyl group, methoxy group, ethoxy group, isopropoxy group and phenoxy group, and these groups may be substituted by a halogen atom, hydroxyl group, aldehyde group, carboxyl group, amino group, isocyanate group, nitro group or sulfone group.

These R groups in the general formula need not be all the same, and optional combination thereof can be taken.

The symbol n in the general formula is not particularly limited, but it is in the range of 1 to 100,000, preferably 1 to 1,000.

Typical examples of the cyclotetrasilanes include decamethyl bicyclo(2.2.0)hexasilane, decaisopropyl bicyclo(2.2.0)hexasilane, dodecamethyl tricyclo(4.2.0.0$^{2,5}$)octasilane, dodecaisopropyl tricyclo(4.2.0.0$^{2,5}$)octasilane, tetradecaisopropyl tetracyclo(6.2.0.0$^{2,7}$.0$^{3,6}$)decasilane and hexadecaisopropyl pentacyclo(8.2.0.0$^{2,9}$.0$^{3,8}$.0$^{4,7}$) dodecasilane,

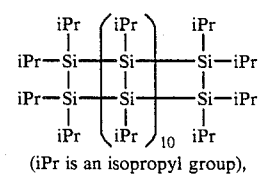

(iPr is an isopropyl group), and

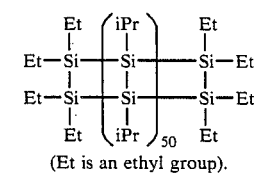

(Et is an ethyl group).

The ladder polysilanes of the present invention are stable, and for example, the reaction of the polysilane with oxygen in air (production of an Si—O bond) is very slow and hence they are easy to preserve and handle. The bulkier the R group in the general formula is, the greater this effect is, which would be attributable to the steric hindrance of the R group. The other practically preferable points of the polysilanes are to be thermoplastic and to be soluble in various organic solvents such as toluene, benzene and tetrahydrofuran.

Now, a method for preparing the polysilanes of the present invention will be described.

Raw materials of the polysilanes are compounds represented by the following formulae (II) and (III):

$$X_2RSiSiRX_2 \quad (II)$$

$$XR_2SiSiR_2X \quad (III)$$

wherein X is a halogen atom, preferably a chlorine atom.

A mixture of the compounds (II) and (III) in a predetermined ratio is first reacted with an alkaline metal or an alkaline earth metal. When the reactants are liquid, the reaction may be performed without any solvent, but usually, a method is employed which makes use of a solvent such as heptane, octane, benzene, toluene, xylene or tetrahydrofurane. Of the alkaline metals and alkaline earth metals, lithium, sodium and magnesium are desirable. Reaction temperature is in the range of $-100°$ to $400°$ C., preferably $0°$ to $300°$ C., and reaction time is in the range of 10 minutes to 50 hours. In the present invention, a treatment process subsequent to the reaction is not particularly limited, but in general, a formed salt is filtered out, washed with water and separated, and afterward the desired product is taken out therefrom. Furthermore, if necessary, purification may be carried out in accordance with a recrystallization process by the use of any of the various solvents, as described in examples given hereinafter. The kind [the value of n in the general formula (I)] and yield of the desired product depend upon reaction conditions and particularly the ratio of the compounds (II) and (III) which are raw materials.

Especially in the case that the polysilane having a high molecular weight [e.g., the value of n in the formula (I) is 5 or more] is demanded, it is preferable that the ratio of the compound (II) of the raw material is heightened in the above-mentioned manufacturing process. In this case, the polysilane obtained by the reaction may be further treated on the terminal portion thereof with the raw material compound (III), an alkyl alkali, an alcohol or water. In addition, it is also possible to obtain substances having different molecular weights by the use of several solvents.

The compounds (II) and (III) which are the raw materials can be prepared through the following process:

(a) The reaction of a metallic silicon with a halogenated hydrocarbon (chloromethane, chlorobenzene or the like), or (b) the reaction of a disilane hexahalide with a Grignard reagent:

(e.g., $Si_2Cl_6 + 2RMgCl \rightarrow RCl_2SiSiCl_2R$)

The process (a) is presently used on an industrially large scale, and in this process, the desired polysilane is produced together with various alkylchlorosilanes. The other process (b) mentioned above is a reaction using $Si_2Cl_6$ which becomes industrially manufactured as a raw material of $Si_2H_6$ the demand of which rapidly increases as a gas for semiconductors (e.g., Japanese Patent Laid-Open Nos. 232910/1984, 207829/1984 and 207830/1984).

The present invention does not intend to particularly limit the process for preparing the compounds (II) and (III) which are the raw materials, but if the just described process is utilized, these compounds are easily available.

As is apparent from the foregoing, the ladder polysilanes of the present invention can be prepared from the easily available raw materials and have excellent physical properties such as thermoplasticity and dissolvability in the solvent.

The polysilanes of the present invention have electric conductivity and photosensitivity (absorption of ultraviolet), and hence attempts are made to utilize them as various functional materials such as photoresists, semiconductors, photosensitive materials for copying machines, initiators for photoreactions, radical initiators and prepolymers for ceramics. Therefore, it is fair to say that the polysilanes of the present case are industrially useful.

Now, the present invention will be described in reference to examples, but it should be understood that these examples explain the present invention but do not intend to restrict its scope.

EXAMPLE 1

In a 200-milliliter flask were placed 0.68 g (2.39 mmol) of $Cl_2(iso-C_3H_7)SiSi(iso-C_3H_7)Cl_2$, 2.15 g (7.18 mmol) of $Cl(iso-C_3H_7)_2SiSi(iso-C_3H_7)_2Cl$, 0.18 g (25.9 mmol) of Li and 100 ml of THF as a solvent, and the solution was then stirred in a nitrogen atmosphere at room temperature for 24 hours to perform reaction. After the reaction had been over, the reaction liquid was passed through a liquid chromatograph to collect a desired product. This product was then purified with acetone by recrystallization, thereby obtaining 47 mg of colorless crystals (yield=3.3%).

The obtained crystals had a melting point of 384° to 395° C., and from results of elementary analysis, the undermentioned $^1H$ NMR, $^{13}C$ NMR and $^{29}Si$ NMR, IR, UV, MS (mass spectrum) and X-ray crystallography, it was confirmed that the structure of the obtained crystals was as follows:

```
      iPr  iPr  iPr
       |    |    |
iPr—Si—Si—Si—iPr
       |    |    |
iPr—Si—Si—Si—iPr
       |    |    |
      iPr  iPr  iPr
      (iPr = iso-C_3H_7)
```

$^1H$ NMR: ($C_6D_6$, $Me_4Si$) δ p.p.m.
1.362–1.804 (—C$\underline{H}$(CH$_3$)$_2$)

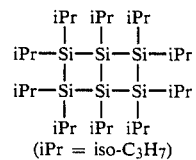

| $^{13}C$ NMR: | p.p.m. | | |
|---|---|---|---|
| | 14.787 | 2C | |
| | 16.037 | 4C | [—$\underline{C}$H(CH$_3$)$_2$] |
| | 17.500 | 4C | |
| | 21.433 | 4C | |
| | 22.379 | 4C | [—CH($\underline{C}$H$_3$)$_2$] |
| | 23.202 | 8C | |
| | 24.177 | 4C | |
| $^{29}Si$ NMR: | p.p.m. | | |

| | |
|---|---|
| −21.22 | (<u>Si</u>—iPr$_2$) |
| −34.24 | (<u>Si</u>—iPr) |

IR(KBr disc): 875 cm$^{-1}$ (Cyclotetrasilane)
UV: $\lambda_{max}$ 310 nm ($\epsilon=971$)
FDMS: m/z 589 parent clusters
598 (M$^+$), 599 (M$^+$+1)
600 (M$^+$+2), 601 (M$^+$+3)
Exact MS: Found: 598.4097
Calcd for C$_{30}$H$_{70}$Si$_6$: 598.4094

| Mass | Intensity | nmu | Elemental Formula |
|---|---|---|---|
| 596.9662 | 0.70 | — | |
| 598.4097 | 4.22 | 0.3 | |
| 599.1284 | 1.20 | — | C$_{30}$H$_{70}$Si$_6$ |

EXAMPLE 2

In a 2-liter flask were placed 21 g (70.4 mmol) of Cl$_2$(iso-C$_3$H$_7$)SiSi(iso-C$_3$H$_7$)Cl$_2$, 20 g (70.4 mmol) of Cl(iso-C$_3$H$_7$)$_2$SiSi(iso-C$_3$H$_7$)$_2$Cl, 3 g (428 mmol) of Li and 1 l of THF as a solvent, and the solution was then stirred in a nitrogen atmosphere at room temperature for 50 hours to perform reaction. After the reaction had been over, a portion of the reaction liquid was passed through a liquid chromatograph to collect a low molecular weight product. This product was then purified with ether and acetonitrile by recrystallization, thereby obtaining about 30 mg of colorless crystals.

The obtained crystals had a melting point of 220° to 248° C., and from results of elementary analysis, the undermentioned $^1$H NMR, UV and MS (mass spectrum), it was confirmed that the structure of the obtained crystals was as follows:

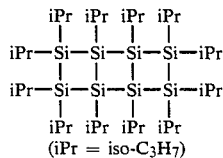
(iPr = iso-C$_3$H$_7$)

$^1$H NMR: (C$_6$D$_6$, Me$_4$Si) δ p.p.m.
1.32–1.90 (—C<u>H</u>(CH$_3$)$_2$)

| $^{13}$C NMR: | p.p.m. | | |
|---|---|---|---|
| | 16.77 | 8C | [—<u>C</u>H(CH$_3$)$_2$] |
| | 10.03 | 4C | |
| | 21.92 | 4C | |
| | 22.40 | 4C | |
| | 22.99 | 4C | |
| | 23.33 | 4C | [—CH(<u>C</u>H$_3$)$_2$] |
| | 23.60 | 4C | |
| | 23.93 | 4C | |
| $^{29}$Si NMR: | p.p.m. | | |
| | −21.28 | (—<u>Si</u>—(iPr)$_2$) | |
| | −32.39 | (—<u>Si</u>—iPr) | |

UV: $\lambda_{max}$ 310 nm ($\epsilon=3400$, 355 nm ($\epsilon=1160$)
FDMS: m/z 740 parent clusters [rel, ints (%)]
740 (M$^+$, 100), 741 (M$^+$+1, 86)
742 (M$^+$+2, 74), 743 (M$^+$+3, 51)
744 (M$^+$+4, 14)

Furthermore, in order to take out a polymeric component from the reaction liquid, the following procedure was taken: To 500 ml of the reaction liquid was added 400 ml of hexane, followed by filtration. Afterward, the filtrate was passed through a neutral alumina column so as to remove the remaining Li therefrom. The used solvent was then removed therefrom to obtain about 1.1 g of a reddish orange solid (A) (number-average molecular weight (Mn)=1,900, weight-average molecular weight (Mw)=3,100 in terms of polystyrene). Then, toluene was added to the hexane-insoluble material, followed by filtration. Afterward, the filtrate was passed through the neutral alumina column, and the solvent was then removed therefrom, thereby obtaining about 600 mg of a reddish orange solid (B) (Mn=4,000, Mw=10,000).

From results of elementary analysis and the undermentioned UV, $^{29}$Si NMR, it was confirmed that the structure of the obtained polysilanes were as follows:

(A) UV $\lambda_{max}$ 315 nm, 410–440 nm;
(B) UV $\lambda_{max}$ 315 nm, 420–460 nm
$^{29}$Si NMR: p.p.m. (A), (B) −58 − −22 (many peaks)

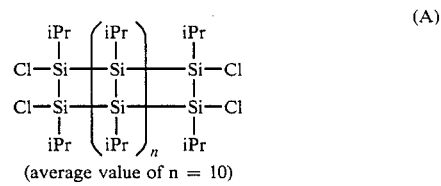
(average value of n = 10)

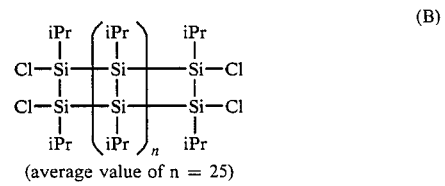
(average value of n = 25)

Moreover, about 150 mg of a reddish orange polysilane (C) (Mn=19,000, Mw=25,000) was taken out from a portion of the reaction liquid by the use of GPC.

From results of elementary analysis and the undermentioned UV, it was confirmed that the structure of the obtained polysilane was as follows:

(C) UV $\lambda_{max}$ 315 nm, 420–460 nm

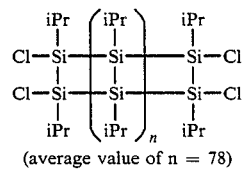
(average value of n = 78)

EXAMPLE 3

In a 2-liter flask were placed 84.0 g (296 mmol) of CL$_2$(iso-C$_3$H$_7$)SiSi(iso-C$_3$H$_7$)Cl$_2$, 600 ml of THF as a solvent and 600 ml of benzene, and 8.2 g (1180 mmol) of Li were added thereto with stirring at 0° C. over 1.5 hours in a nitrogen atmosphere. The solution was then stirred at room temperature for 20 hours to perform reaction. The used solvent was distilled under reduced pressure off from the reaction mixture, and then 600 ml of hexane were added to the residue, followed by filtration. In order to remove the remaining Li, the filtrate was then passed through a neutral alumina column, and afterward the solvent was further removed therefrom, thereby obtaining 31.9 g (yield=69.9%) of an orange solid (D) (Mn=1,400, Mw=2,500 in terms of polystyrene). Then, 300 ml of toluene were added to the hexane-insoluble material, followed by filtration. Afterward, the filtrate was passed through the neutral alumina column, and afterward the solvent was removed therefrom, thereby obtaining 13.8 g (yield=31.1%) of a reddish orange solid (E) (Mn=2,900, Mw=7,600).

From results of elementary analysis and the undermentioned UV, it was confirmed that the structures of the obtained polysilane were as follows:

(D) UV $\lambda_{max}$ 315 nm, 410–430 nm;
(E) UV $\lambda_{max}$ 315 nm, 420–460 nm

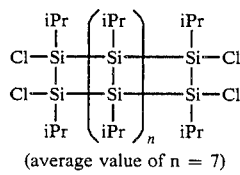

(average value of n = 7)

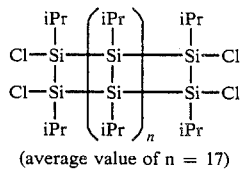

(average value of n = 17)

EXAMPLE 4

In a 500-milliliter flask were placed 16.19 g (57 mmol) of Cl$_2$(iso-C$_3$H$_7$)SiSi(iso-C$_3$H$_7$)Cl$_2$, 1.60 g (230 mmol) of Li and 230 ml of THF as a solvent, and the solution was then stirred at room temperature for 108 hours in a nitrogen atmosphere to perform reaction. Afterward, 6.2 g (57 mmol) of (CH$_3$)$_3$SiCl was added to the reaction solution, and the latter was further stirred at room temperature to carry out the reaction. The used solvent was distilled off from the reaction mixture under reduced pressure, and then 100 ml of toluene was added to the residue, followed by filtration. The filtrate was then passed through a neutral alumina column, and afterward the solvent was further removed therefrom, thereby obtaining 7.4 g (yield=57.0%) of a yellow polymer (F) (Mn=780, Mw=910).

From results of elementary analysis and the undermentioned UV, it was confirmed that the structure of the obtained polysilane was as follows:

(F) UV $\lambda_{max}$ 310 nm, 370–400 nm

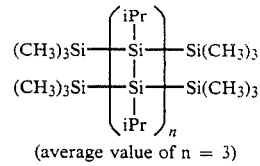

(average value of n = 3)

According to the present invention, there can be provided novel ladder polysilanes which are industrially useful and future applications of which are expected, and a method for preparing the ladder polysilanes can also be provided. These polysilanes may be prepared by the economical method, since starting materials are relatively easily available.

What is claimed is:

1. A ladder polysilane represented by the general formula (I):

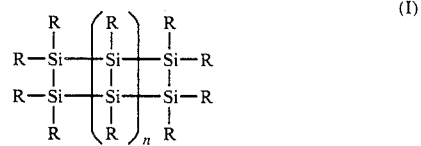

where n is a positive integer, and R is a halogen atom, a hydrogen atom, a hydroxyl group, an alkyl group, an alkenyl group, an aryl group or an alkoxy group having 20 or less carbon atoms, and said alkyl, alkenyl, aryl or alkoxy group may contain a functional group selected from the group consisting of —COOH, —SO$_3$H, —NH$_2$, —NO$_2$, —NCO, —F, —Cl, —Br, —I or —OH.

2. A method for preparing said ladder polysilane described in claim 1 which comprises the step of reacting a mixture of disilane compounds represented by the general formulae X$_2$RSiSiRX$_2$ and XR$_2$SiSiR$_2$X wherein X is a halogen atom with an alkaline metal or an alkaline earth metal.

3. A method for preparing said ladder polysilane described in claim 1 which comprises the step of reacting a disilane compound represented by the general formula X$_2$RSiSiRX$_2$ wherein X is a halogen atom with an alkaline metal or an alkaline earth metal.

* * * * *